United States Patent [19]

Maggi

[11] Patent Number: 4,466,425
[45] Date of Patent: Aug. 21, 1984

[54] OPERATING TABLE FOR OPHTHALMIC SURGERY

[76] Inventor: Carlo Maggi, 8 Via Latina, 00179 Roma, Italy

[21] Appl. No.: 338,147

[22] Filed: Jan. 8, 1982

[30] Foreign Application Priority Data

Jan. 20, 1981 [IT] Italy .............................. 47599 A/81

[51] Int. Cl.$^3$ ............................................ A61B 19/00
[52] U.S. Cl. .................................. 128/1 R; 269/325; 269/328
[58] Field of Search ................. 128/1 R, 1 B, 202.12, 128/202.13, 202.16, 202.18, 24 R; 604/313, 315; 269/322–328

[56] References Cited

U.S. PATENT DOCUMENTS

| | | | |
|---|---|---|---|
| 3,034,843 | 5/1962 | Moon | 269/322 |
| 3,392,723 | 7/1968 | Calvin | 128/24 R |
| 3,813,092 | 5/1974 | Foster | 269/322 |
| 3,858,570 | 1/1975 | Beld et al. | 128/1 B |
| 4,018,217 | 4/1977 | Evans | 128/303 R X |
| 4,058,112 | 11/1977 | Johnson | 128/1 R |
| 4,131,802 | 12/1978 | Braden et al. | 269/322 X |
| 4,202,676 | 5/1980 | Pelosi, Jr. et al. | 128/1 R X |
| 4,367,728 | 1/1983 | Mutke | 128/1 R |

OTHER PUBLICATIONS

Schimek, R. A. et al., "Ocular Compressor and Fixator" Presented as a New Instrument at the Seventy-Fifth Annual Meeting of the Amer. Acad. of Ophthalmology and Otolaryngology, Las Vegas, Nev. Oct. 5–9, 1970.

Primary Examiner—C. Fred Rosenbaum
Assistant Examiner—Michelle N. Lester

[57] ABSTRACT

An operating table for ophthalmic surgery consisting of a base, held at an adequate height from the floor by supporting members, and on which a stretcher is placed which is movable in the longitudinal sense and adjustable in height, one end of which is connected to an adjustable assembly comprising a first device for positioning the patient's head, with the body being on said stretcher, in the position most convenient for carrying out the surgical operation and a second device supporting a mask element provided with an opening in which the eye to be operated on is adapted and on the edge of which the orbital edge of said eye is sealed. A transparent rigid airtight cover is provided which may be adapted on said base plane in such a way as to create an airtight environment apt to be appropriately depressurized through conventional vacuum means, said airtight environment completely surrounding the body of the patient with the exception of the eye to be operated on, which through said opening in said mask element appears exposed to the pressure of the outside ambient.

8 Claims, 5 Drawing Figures

OPERATING TABLE FOR OPHTHALMIC SURGERY

This invention refers to an operating table for the surgery of the eye.

The eyeball in its external configuration has a shape which resembles that of an approximately spherical body with semi-rigid walls, having an internal pressure or tension about 20 mm Hg higher than the normal atmospheric pressure.

The eyeball (with its adnexae) is contained in a bony cavity of the skull (the orbit), having a conformation which is essentially that of a conical aperture. The arterial blood supply is provided by a single artery (the ophthalmic artery) whose flow is directed almost totally to the eyeball.

The surgical opening of the ocular wall causes a fall to zero of the intraocular pressure, diminished venous outflow and increased arterial inflow to the eye, resulting in an increase in the ocular contents, which consequently tend to extrude through the said opening.

As a result, surgical operations involving the opening of the eyeball, performed up to the present time at normal atmospheric pressure, cause more or less immediately the congestion of the choroid and consequent swelling, with a tendency to the extrusion of the intraocular tissues.

In order to reduce these undesirable effects, various systems have been devised, unfortunately with scarse results, such as that of reducing the patient's arterial blood pressure by means of general medication, which as well as giving unsatisfactory results, can have a harmful effect on the patient's physical condition; or by exerting pre-operative pressure on the eyeball to increase the normal elimination of the aqueous humour by means of the normal excretory channels and thus reducing the intraocular contents (which however are rapidly regenerated), and all similar expedients which however oblige the surgeon to abbreviate the operation as far as possible.

The object of the present invention is to provide an operating table for ophthalmic surgery designed in such a way as to allow the positioning of the patient's body in an enclosed environment which is hermetically sealed so as to permit depressurisation with the sole exclusion of the orbit containing the eye to undergo surgery, which remains subject to normal atmospheric pressure. By using the operating table just mentioned it is possible to obtain a differentiated pressure between the body inside said depressurised environment and the orbital contents exposed to the outside pressure.

If the so obtained pressure inside said depressurised environment is 20 mm Hg (equivalent to normal intraocular tension) less than the external pressure, compression of the exposed orbital area will be caused resulting in pressure on the vascular system of the eye equal to that previously exerted by the normal intraocular tension (before surgical opening), while the general blood pressure remains apparently unchanged expressing a difference in pressure between the blood vessels of the whole body and its external pressure on the inside of said depressurised environment equal to that it had previously maintained with respect to the atmospheric pressure before being subjected to depressurisation It is therefore a case of establishing a pressure difference at least equal to the value of the intraocular pressure of the patient to be operated on, between the orbital area of about 40 cm$^2$, and the entire remaining body surface area, variable with the size of the patient between 10,000 and 20,000 cm$^2$, entirely contained inside the enclosed environment and exposed therefore to depressurisation.

The difference in area between the two surfaces at different pressures, one at normal atmospheric pressure and the other at a lower pressure, is so enormous as to be incapable of triggering any compensation which would theoretically be possible with an increase in the patient's arterial pressure either locally or generally, and the resultant orbital compression with the relative intraoperative advantages lasts as long as such pressure difference lasts without any time limit as demonstrated by experience.

As results from the foregoing, by the adoption of the operating table according to the present invention in surgical operations on the eye, even while the eyeball is opened the intraocular tissues receive the same pressure as with the eyeball intact, without therefore the occurrence of alterations in the hydrodynamics of the haematic flow and an increase in the contents of the eyeball.

Finally it must be noted that the rigid bony walls of the orbit will prevent the previously mentioned difference in pressure between the said depressurised environment and the external ambient from involving the neighbouring tissues and relative vascular network.

The present invention will be illustrated in more detail as follows by the description of a preferred embodiment thereof, given by way of example and not to be limiting, taken along with the enclosed drawings.

Figure 1:
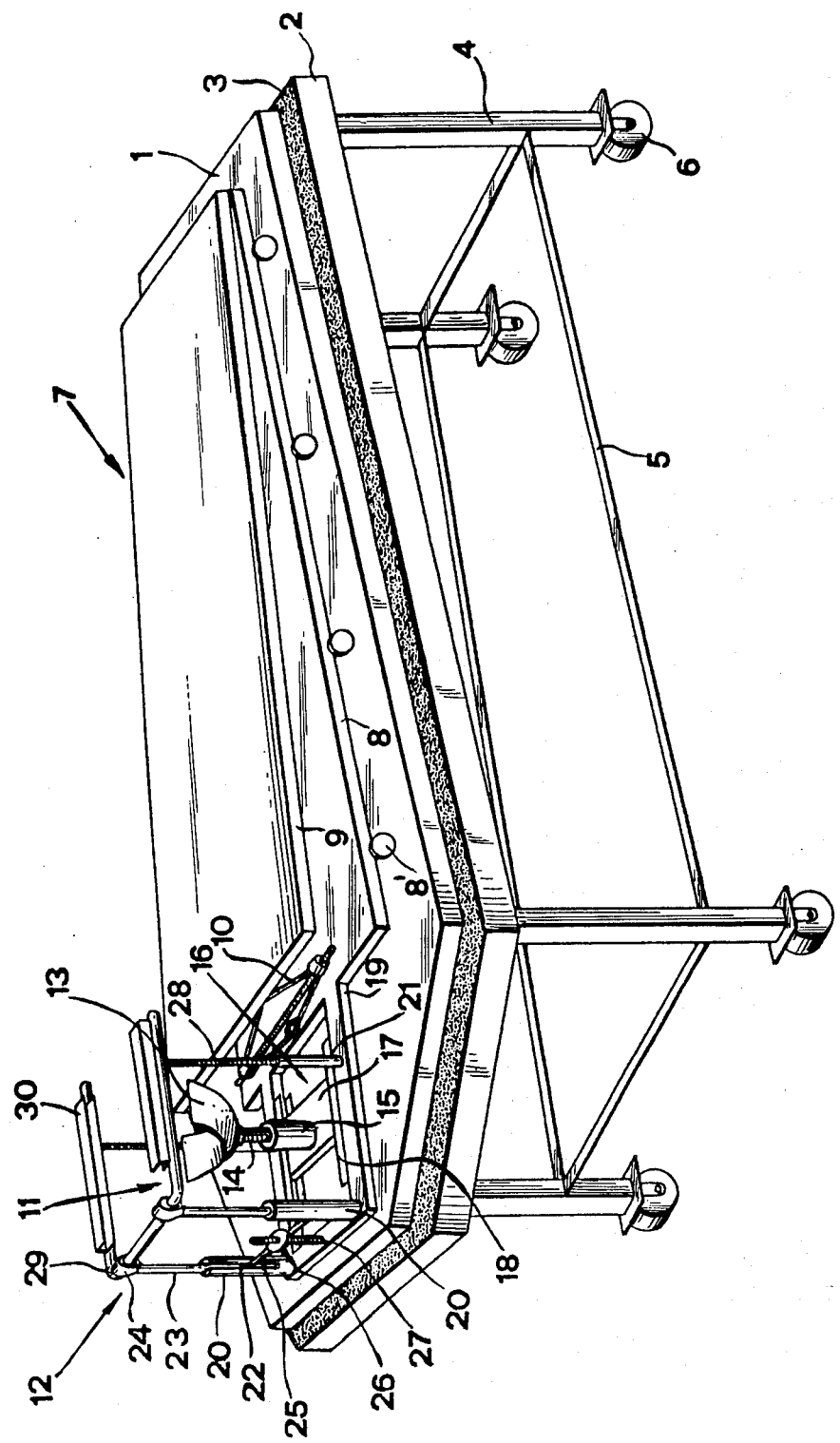
FIG. 1 is a perspective view of the base plane of the operating table according to the invention, supporting a stretcher connected to an adjustable assembly for the positioning of the patient's head.

With reference to FIG. 1, the numeral 1 indicates the base plane of the operating table according to the invention showing a perimetrical step 2 the surface of which is covered with compressible material 3, for example rubber, for reasons to be clarified further on.

Base plane 1 is supported at an adequate distance from the floor by means of four legs 4 connected by bracing bars 5, longitudinal and transversal, and each equipped at its free end with orientable wheel 6.

On base plane 1 a stretcher is placed, generally indicated in 7, on which the body of the patient to be operated on is laid.

Stretcher 7 is composed of two plane surfaces one over the other, of which 8 is the lower one and the other, 9, the upper one, hinged at one end, precisely the one related to the position of the patient's feet, and equipped at the opposite end, which provides support for the patient's shoulders, with a pantograph screw jack 10 manually actuated and apt to place the upper plane surface 9 of stretcher 7 according to a desired inclination with respect to the lower plane surface 8 which is equipped with eight wheels 8', four on each side, for easy sliding of stretcher 7 in a longitudinal direction on base plane 1.

The free end of the lower surface 8 of stretcher 7 is integral with the base frame of an adjustable assembly for positioning the patient's head in the most appropriate position for carrying out the surgical operation and comprising a first device, generally indicated in 11, for positioning the head of the patient, and a second device, indicated generally in 12, for adjusting the position of a special rigid mask element to be described later, serving the purpose of isolating the head of the patient from the outside environment with the exclusion of the orbital region to undergo surgery.

Figure 2:
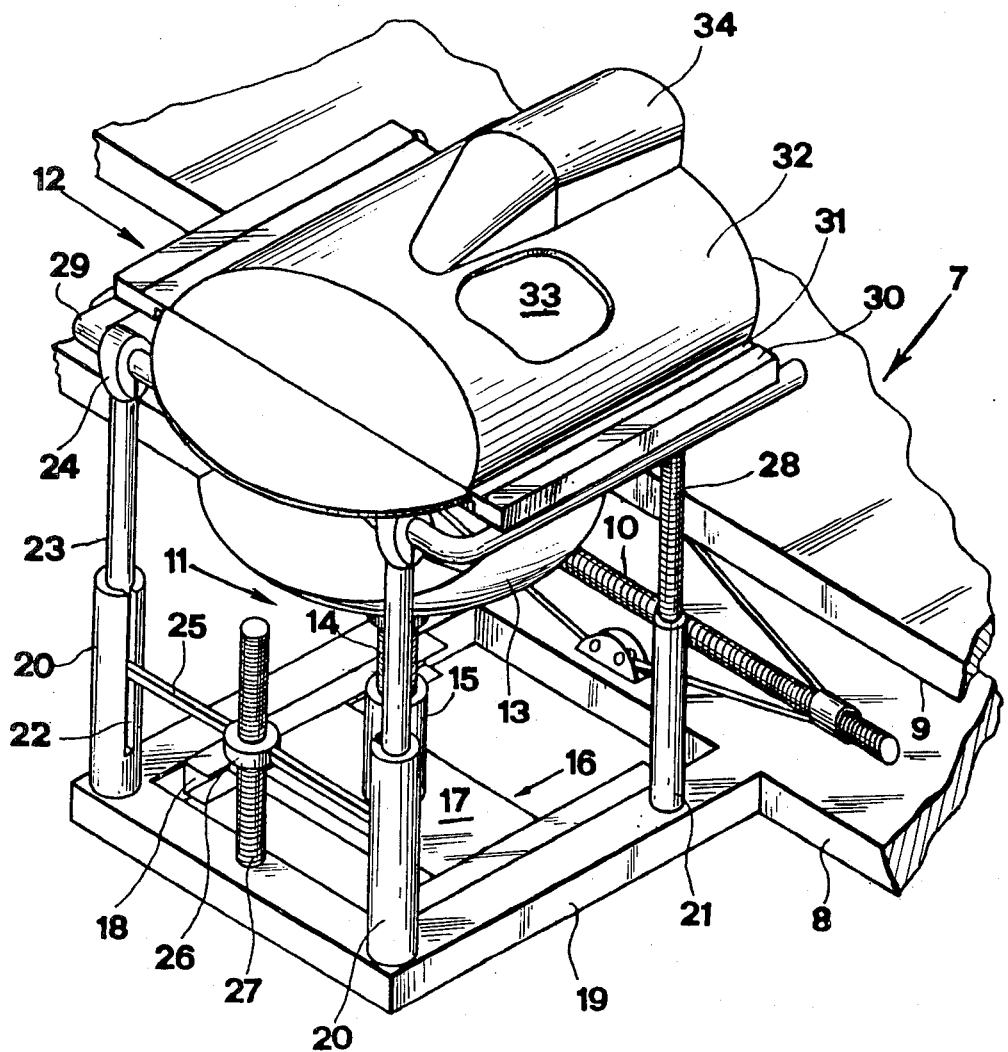
FIG. 2 is a perspective view showing the detail of the adjustable assembly for positioning the head of the patient, including a mask element.

Observing also FIG. 2 in which the adjustable assembly mentioned above is illustrated more in detail in an enlarged scale and completed with the said mask element, it can be noticed that the device 11 for positioning the patient's head comprises a head rest 13 shaped as a saddle, appropriately padded on its inner surface, supported in a central position by the upper end, freely pivotable in a special bushing integral with the head rest 13, of an externally threaded vertical rod 14, in engagement with the internal thread of the axial hole of a cylindrical small supporting block 15, the lower end of which is fixed at the center of a sliding member, generally indicated in 16, formed by a cross-bar 17 provided on each end with a slider 18, formed by a U-shaped element. The outside surface of the rib thereof is apt to slide on the internal surface of a respective longitudinal side of base frame 19 integral, as previously stated, with the side of the free end of the lower plane surface 8 of stretcher 7 with which it forms a rectangle.

With the above mentioned arrangement, the head rest 13 may be moved upwards or downwards respectively by unscrewing or screwing the threaded vertical rod 14 in the corresponding thread of the axial hole of the small supporting block 15 and also back and forth by sliding in one sense or the other the sliders 18 on the respective sides of base frame 19.

The device 12 for the adjustment of the position of said mask element comprises four studs, of which two, 20, are in the front and two, 21, in the back, vertically fixed to the base frame 19. Each of the front studs 20 is formed by a cylindrical body having an axial hole therethrough and presenting a channel 22 extending along a generatrix almost up to the lower end, channels 22 of the two opposed studs 20 being arranged so as to be one facing the other on the same plane.

In the axial holes of the front studs 20 are slidably fitted respective non-threaded vertical rods 23 in the form of cylindrical bars each of which terminates at the upper end with an eyehole 24 while the terminal lower part is integral perpendicularly with an arm 25 extending to the outside through the respective channel 22 till it is fixed to the perimetrical surface of an annular small block 26, the axial threaded hole of which is in engagement with the corresponding outside thread of a vertical bar 27 free to rotate, resting on the plane of the forward transversal side of base frame 19, in equidistant position with respect to the two front studs 20.

In each of the rear studs 21, formed by a cylindrical body, an axial threaded hole is formed, wherein a vertical rod 28 provided with corresponding external thread is in engagement, the upper end of which is integral with an axial (not shown) non-threaded small cylinder.

In eyeholes 24 of the non-threaded vertical rods 20 the transversal side of a U-shaped frame 29 having a circular transversal section is pivotally supported, the parallel longitudinal arms of which present at the free terminal parts closed slots (not shown) apt to pivotally receive said axial non-threaded small cylinders on the upper ends of the respective threaded vertical rods 28.

Above each of said longitudinal parallel arms of the U-shaped frame 29 a guide 30 is fixed having a groove apt to slidingly receive and support a respective side wing 31 of a mask 32 of rigid, transparent material for the protection of the patient's head, as will be made clear more in detail further on, presenting an opening 33, which is to coincide, in its application, with the orbital edge of the eye to undergo surgery, as well as a hollow protrusion 34 in coincidence with the part of the mouth and nose of the patient itself for positioning of the end part of the flexible tube of the anaesthetic apparatus.

Figure 3:
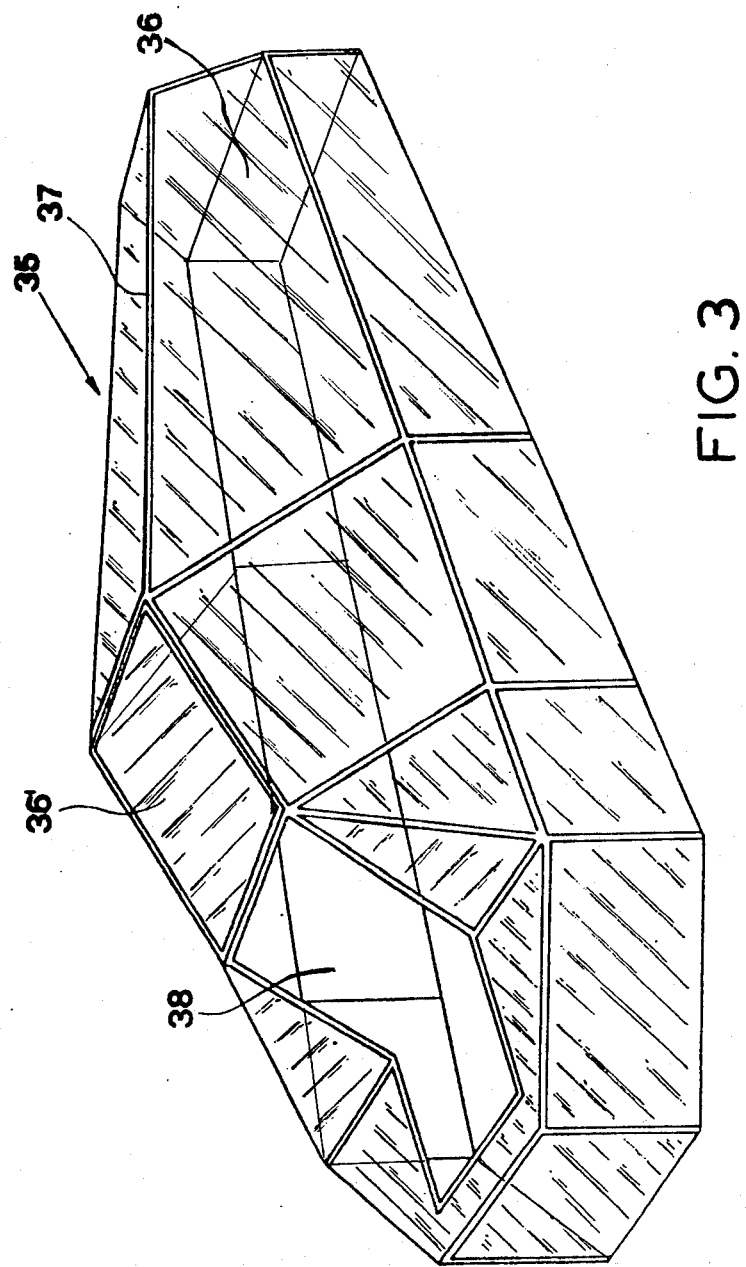
FIG. 3 is a perspective view of the rigid cover to be applied over the base plane of FIG. 1 for creating an airtight environment.

In FIG. 3 a rigid cover, or pneumatic bell, is shown, generally indicated in 35, apt to create an airtight environment around the body of the patient when applied on the base plane 1, as will be further explained later.

The rigid cover 35 presents a base perimeter having the same shape and essentially the same dimensions of step 2 of base plane 1.

Cover 35 is formed by a series of panels 36 of transparent, airtight material, fixed on a supporting framework 37, and at least one of said panels 36, placed in appropriate position, for example the one indicated in 36' (see also FIG. 4) is openable being hinged on one side, in order to allow, if required, a rapid access to the patient's body when same is enclosed on the inside of bell 35.

The front part of cover 35, and more precisely that part which after the cover 35 itself has been mounted appears to be in coincidence of said adjustable assembly for positioning and blocking the head of the patient, is provided with an angled window 38, having no closing panel, and equipped with a movable frame 39 (see FIG. 4) having the same shape, hinged at its upper side to the adjacent side of the framework 37.

Figure 4:
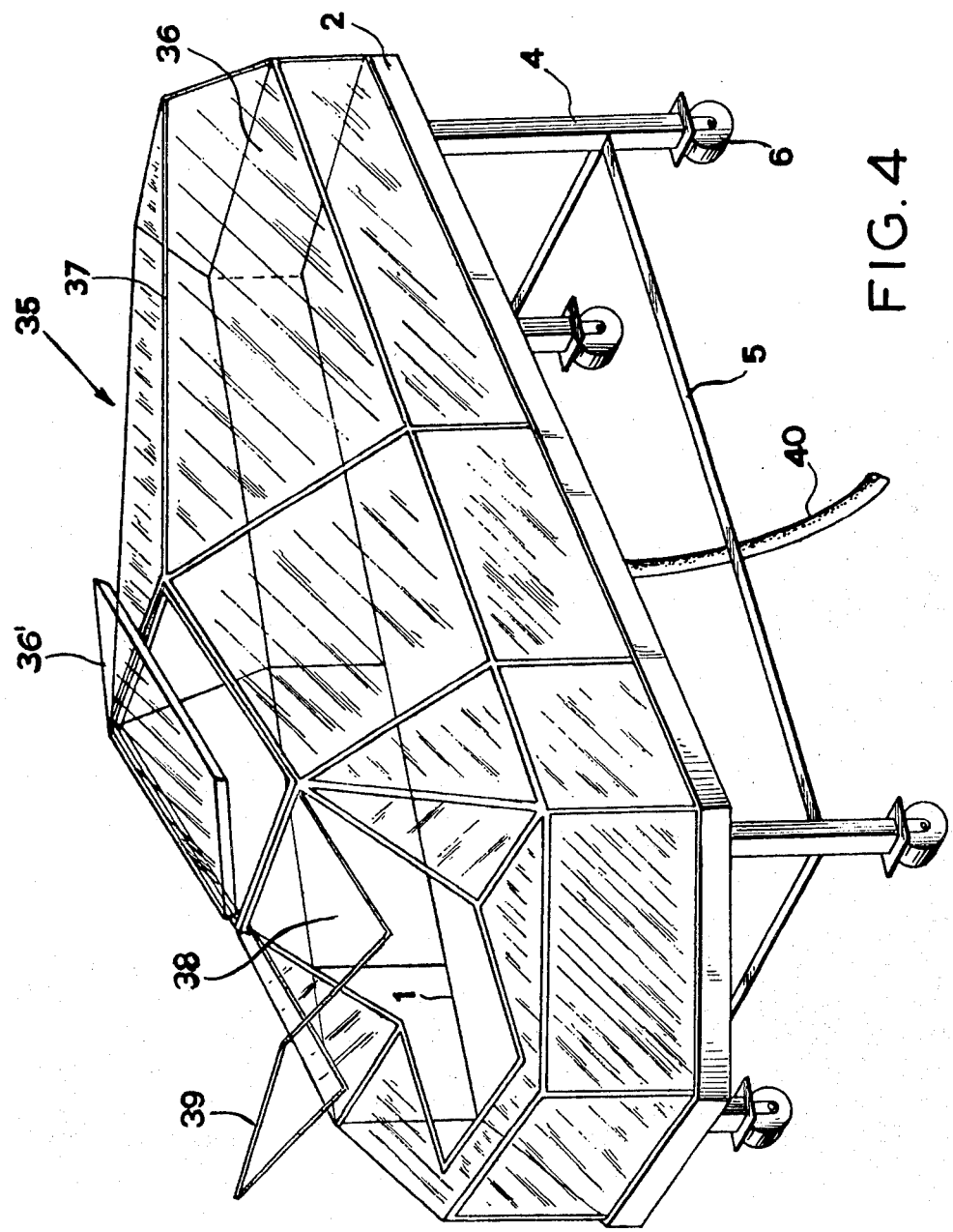
FIG. 4 is a perspective view of the baseplane of FIG. 1 with the rigid cover of FIG. 3 applied thereon.

In FIG. 4 the cover 35 can be seen in its operating position with its perimetrical base edge installed on the gasket 3 of yielding material which covers step 2 of baseplane 1 in such a way as to create an airtight joint. In the above mentioned figure a flexible tube 40 can also be seen, partially represented, one end of which is connected to a connector (not shown) communicating in an airtight way with the inside of the environment created with the application of bell 35 on base plane 1 while the other end is connected to a conventional suction apparatus (not shown).

Figure 5:
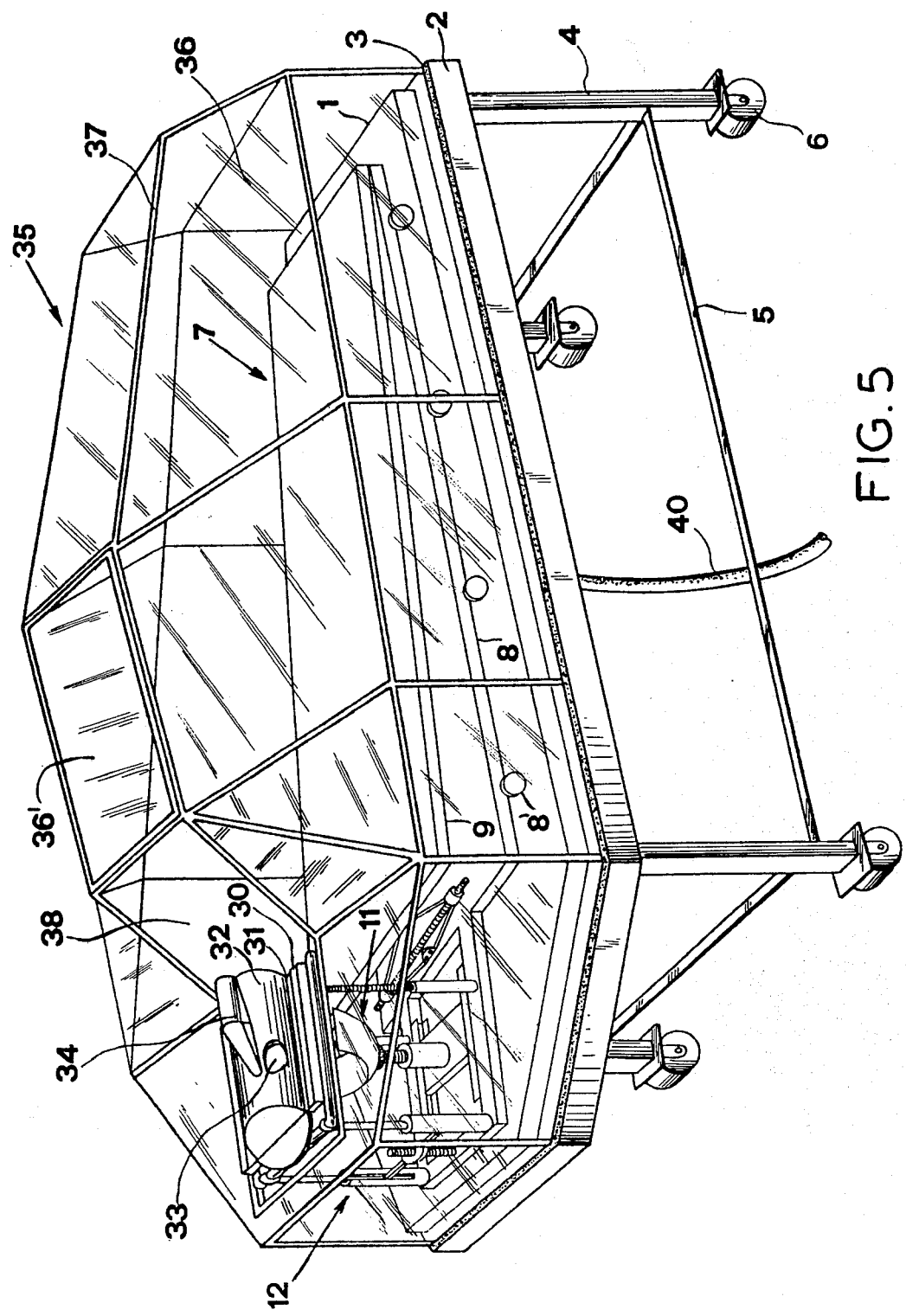
FIG. 5 is a perspective view of the complete operating table according to the invention.

The operating table according to the present invention once completed is ready for use and appears as illustrated in FIG. 5.

In order to carry out the surgical operation on the eye in optimum conditions with the use of the operating table according to the invention (FIG. 5), before mounting cover 35 the patient is placed with the head on the head-rest 13 and the body on the upper plane surface 9 of stretcher 7, moved in the most convenient position by sliding on base plane 1 by means of wheels 8'. Then the shoulders of the patient are brought to the appropriate height in relation to the somatic characteristics and to the final position which will have to be taken up by the head, acting on pantograph screwjack 10 in order to incline more or less the upper plane surface 9 with respect to the lower surface 8 of stretcher 7. Then, through device 11, the position of the head is adjusted in height, by screwing or unscrewing in the small supporting block 15 the threaded vertical rod 14, which supports the head-rest 13, and in the longitudinal sense, by means of sliding of slider 16 back or forwards; then the head is held in the desired position by means of device 12 by acting on threaded bar 27 to raise or lower the non-threaded vertical rods 23, with the consequent raising or lowering of the transversal side of U-shaped frame 29 which rotates in eyelets 24, and at the same time on threaded vertical rods 28 in order to raise or lower the longitudinal arms of said U-shaped frame 29 till the transparent mask 32, supported by said U-shaped frame, is brought in close vicinity to the patient's face, with the eye to be operated on in coincidence of opening 33 the edge of which will surround as accurately as possible the edge of the orbit. The cover 35 is then mounted, in the previously described manner, with the openable panel 36' sealingly closed. Movable frame 39 of bell 35 is then raised (see FIG. 4) and a cloth of transparent airtight material is placed over window 38, which cloth will also cover the mask 32 protruding from said window 38, as can be noticed from FIG. 5.

Movable frame 39 is then brought back into the lowered position (see FIG. 3 and 5) so as to sealingly block said airtight transparent cloth on window 38 of cover 35 and a hole of appropriate size is cut on said cloth in coincidence with opening 33 in mask 32, the edge of said hole being sealed with adhesive tape or the like to the area surrounding said opening 33, the edge of which is in turn sealed, with adhesive tape or the like, to the orbital edge of the eye to undergo surgery.

At this point the body of the patient results to be enclosed in an airtight environment with only the eyeball to undergo surgery exposed to the outside pressure, whereby actuating said suction apparatus it will be possible to create in said airtight environment such a depression as to compensate for the intraocular pressure fall, due to the incision of the eyeball, with the difference in pressure in favour of the outside ambient, which, as previously stated, will exert on the vascular system of the exposed eye the same pressure which the intraocular pressure exerted before the incision. As already stated, the anaesthesia can if so desired take place through appropriate flexible tube (not shown) which, inserted in cover 35 through a special airtight connector (not shown) will end at the hollow protrusion 34 of mask 32 in coincidence of the mouth and nose of the patient.

This invention also contemplates the possibility of fitting the cover 35 on a conventional operating table both on the plane thereof as well as allowing the cover itself to descend down to the floor with the conventional operating table inside, obviously providing appropriate airtight sealing means.

Moreover, the mask 32 can directly form part of the cover 35, in which case there is only one opening (i.e. the one in the mask 32) since said cloth with its hole is superfluous; it would also be conceivable to construct an operating table with the cover directly provided with the opening or hole to be sealed around the orbital edge of the eye.

This invention is not limited to the examples of embodiment described but comprises any variation of execution thereof.

I claim:

1. An operating table for ophthalmic surgery, comprising a base member for supporting the patient to be operated on; a cover member, airtight mounted with respect to said base member and adapted to enclose the entire body of said patient; aperture means disposed in said cover member and adapted to encircle the eye to be operated on, the edge of said aperture means being further adapted to be sealed around the orbital edge of the eye of the patient such that the patient's entire body, excluding the orbital region may be subjected to a difference in pressure with respect to the atmospheric pressure, said difference in pressure acting on the exposed orbital area so as to exert a compression in the vascular system of the eye, when surgically opened, equal to that which the intraocular pressure exerted prior to the eye being opened.

2. The operating table according to claim 1, wherein said aperture means includes a face mask element located at the end of said cover member corresponding to the face of the patient, said mask being provided with an aperture adapted to seal around the orbital edge of the eye to be operated on.

3. The operating table according to claim 2, wherein the base member is supported at an adequate distance from the ground, said base member being provided on its upper surface with a stretcher assembly upon which the body of the patient to be operated on is placed, said stretcher assembly being movable in the longitudinal direction, as well as adjustable in inclination with respect to said base member, said stretcher assembly being connected to a first adjustable means for positioning the head of the patient both longitudinally and in height and to a second adjustable means for positioning said face mask element, wherein said cover member is provided with a window located at the position of said first and second adjustable means, said window being sealable by means of an airtight cloth, and said cloth being provided with an aperture which coincides with the aperture located in said face mask element, the edge of said aperture in the cloth being adapted to seal around the edge of said aperture in the face mask member.

4. The operating table according to claim 3, wherein said stretcher assembly comprises upper and lower surface members, said upper and lower surface members being hinged at one of their ends and provided at their other ends with an adjustment means for inclination of said upper surface member with respect to said lower surface member, said lower surface member being provided with wheels for sliding said stretcher assembly in the longitudinal direction with respect to said base member, said lower surface member being integral, at said other end, with a supporting frame for said first and second adjustable means.

5. The operating table according to claim 4, wherein said first adjustable means comprises a head rest, said head rest being attached to and supported by an externally threaded rod member, said rod member adapted to cooperate with an internally threaded supporting block element to adjust the height of said head rest, said internally threaded block element being fixed to a slider member which is adapted to slide back and forth in the supporting frame which is integral with said lower surface member of the stretcher assembly.

6. The operating table according to claim 4, wherein said second adjustable means comprise a plurality of support studs, said studs being adjustable in height, said studs being fixably attached at their lower ends to the support frame integral with the lower surface member of said stretcher assembly and said studs supporting at the top thereof a U-shaped frame member for holding said face mask member.

7. The operating table according to claim 3, wherein said mask member is provided with a hollow protrusion adapted to receive the terminal end of the flexible tube of an anaesthetic apparatus, said hollow protrusion being positioned on said face mask so as to coincide with the mouth and nose of the patient.

8. The operating table according to claim 2, wherein said cover is provided with at least one airtight hatch adapted to give direct access to the patient's body.

* * * * *